(12) United States Patent
Brenzel et al.

(10) Patent No.: US 8,882,787 B2
(45) Date of Patent: Nov. 11, 2014

(54) TISSUE ANCHOR APPARATUS

(75) Inventors: Michael P Brenzel, St. Paul, MN (US);
Theodore P Dale, Minneapolis, MN (US); David M Costello, Waconia, MN (US); Paul J Hindrichs, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1475 days.

(21) Appl. No.: 11/361,197

(22) Filed: Feb. 23, 2006

(65) Prior Publication Data

US 2006/0196137 A1   Sep. 7, 2006

Related U.S. Application Data

(60) Provisional application No. 60/658,194, filed on Mar. 2, 2005.

(51) Int. Cl.
| | |
|---|---|
| *A61B 17/08* | (2006.01) |
| *A61B 19/00* | (2006.01) |
| *A61B 17/00* | (2006.01) |
| *A61B 17/3205* | (2006.01) |

(52) U.S. Cl.
CPC ....... *A61B 19/54* (2013.01); *A61B 2017/00986* (2013.01); *A61B 17/32053* (2013.01); *A61B 2017/00575* (2013.01); *A61B 2017/00243* (2013.01); *A61B 2017/00623* (2013.01)
USPC .......................................... 606/151; 604/107

(58) Field of Classification Search
USPC ............. 606/213, 216, 232, 32, 53, 151, 157, 606/158; 411/32; 607/126, 27; 604/104–108
See application file for complete search history.

(56) References Cited

U.S. PATENT DOCUMENTS

| | | | | | |
|---|---|---|---|---|---|
| 4,274,324 | A | * | 6/1981 | Giannuzzi | 411/38 |
| 5,257,975 | A | * | 11/1993 | Foshee | 604/105 |
| 5,456,667 | A | * | 10/1995 | Ham et al. | 604/107 |
| 5,501,695 | A | * | 3/1996 | Anspach et al. | 606/232 |
| 5,853,422 | A | * | 12/1998 | Huebsch et al. | 606/213 |
| 6,022,373 | A | * | 2/2000 | Li | 606/232 |
| 6,074,416 | A | | 6/2000 | Berg et al. | |
| 6,113,609 | A | * | 9/2000 | Adams | 606/139 |
| 6,171,319 | B1 | * | 1/2001 | Nobles et al. | 606/151 |
| 6,231,561 | B1 | * | 5/2001 | Frazier et al. | 604/500 |
| 6,328,758 | B1 | * | 12/2001 | Tornier et al. | 606/232 |
| 6,461,320 | B1 | * | 10/2002 | Yencho et al. | 604/8 |
| 6,660,008 | B1 | * | 12/2003 | Foerster et al. | 606/327 |
| 6,893,418 | B2 | * | 5/2005 | Liu | 604/106 |

(Continued)

FOREIGN PATENT DOCUMENTS

WO          WO 98/47430          10/1998

*Primary Examiner* — Dianne Dornbusch
*Assistant Examiner* — Alexander Orkin
(74) *Attorney, Agent, or Firm* — Lerner, David, Littenberg, Krumholz & Mentlik, LLP (57) ABSTRACT

A structure that can be used to provide an anchor in or adjacent to a patient's soft body tissue (rather than bone) includes an annular array of flexible members that extend between two axially spaced but aligned tubular members. The space between the tubular members can be selectively changed to affect the amount by which portions of the flexible members between the tubular member project radially outward relative to the tubular members. When the flexible members project radially out, the structure resists axial movement relative to adjacent tissue and therefore acts as an anchor. When the flexible members do not project radially out, they permit axial movement of the structure through adjacent tissue.

12 Claims, 10 Drawing Sheets

(56) References Cited

U.S. PATENT DOCUMENTS

| | | | |
|---|---|---|---|
| 7,097,653 | B2 | 8/2006 | Freudenthal et al. |
| 7,149,587 | B2 * | 12/2006 | Wardle et al. .................. 607/126 |
| 7,713,282 | B2 * | 5/2010 | Frazier et al. ................... 606/200 |
| 8,257,389 | B2 * | 9/2012 | Chanduszko et al. ......... 606/213 |
| 2001/0041858 | A1 | 11/2001 | Ray et al. |
| 2001/0047187 | A1 | 11/2001 | Milo et al. |
| 2002/0042628 | A1 | 4/2002 | Chin et al. |
| 2002/0072768 | A1 * | 6/2002 | Ginn .............................. 606/213 |
| 2003/0078616 | A1 | 4/2003 | Ginn et al. |
| 2003/0236536 | A1 * | 12/2003 | Grigoryants et al. .......... 606/151 |
| 2005/0043759 | A1 * | 2/2005 | Chanduszko .................. 606/213 |
| 2005/0075665 | A1 | 4/2005 | Brenzel et al. |
| 2005/0119675 | A1 * | 6/2005 | Adams et al. .................. 606/151 |
| 2005/0273135 | A1 * | 12/2005 | Chanduszko et al. ......... 606/213 |
| 2006/0122647 | A1 * | 6/2006 | Callaghan et al. ............. 606/213 |

* cited by examiner

TISSUE ANCHOR APPARATUS

This application claims the benefit of U.S. provisional patent application No. 60/658,194, filed Mar. 2, 2005, which is hereby incorporated by reference herein in its entirety.

BACKGROUND OF THE INVENTION

This invention relates to tissue anchors, such as those that can be used in soft tissue at remote locations in a patient's body.

Various medical procedures may benefit from first being able to provide a secure anchor in tissue at a remote location in a patient's body. For example, a percutaneous procedure that involves passing through the septum between two chambers of a patient's heart may benefit from first being able to anchor to the septal tissue. After that has been done, additional instrumentation can be introduced into the patient for operation at other locations having known positions relative to the anchor site. At the conclusion of the procedure it may be desired to remove the tissue anchor from the patient.

Because of their potential importance, improvements to tissue anchor structures and apparatus are always being sought.

SUMMARY OF THE INVENTION

In accordance with the present invention, a selectively operable tissue anchor may include first and second, axially spaced but aligned tubular members, a plurality of flexible members extending between the tubular members, and means for selectively changing the axial spacing between the tubular members to cause or otherwise affect the amount of projection of portions of the flexible members between the tubular members radially outwardly with respect to the tubular members. When the above-mentioned portions of the flexible members are projecting radially out, they inhibit axial motion of the structure relative to tissue that is adjacent to those members. For example, the flexible members may be embedded in the adjacent tissue or they may abut a surface of the adjacent tissue. On the other hand, when the above-mentioned portions of the flexible members do not project radially out, they permit axial motion of the structure relative to adjacent tissue.

The flexible members may form an array that is annular about a central longitudinal axis that extends between the tubular members. Each flexible member may spiral about that axis.

The means for selectively changing the spacing between the tubular members may include a linking member that extends between the tubular members inside an annular array of the flexible members. The linking member may be secured to one of the tubular members and may be axially slidable within and relative to the other tubular member. The apparatus may further include means for selectively fixing at least one axial position of the linking member relative to the tubular member that it is otherwise slidable relative to.

The flexible members may be resiliently biased to extend between the tubular members without significant radial outward projection from the tubular members. Alternatively, the flexible members may be resiliently biased to project radially outward from the tubular members.

The apparatus may include a tissue penetrating structure on an end of one of the tubular members that is remote from the flexible members.

At least the portion of the apparatus that includes and is adjacent to the flexible members may be configured for delivery into a patient via a body conduit of the patient. For example, that body conduit may be a portion of the patient's blood circulatory system. The portion of the apparatus that is thus deliverable into the patient may be configured for delivery over a guide wire previously introduced into the patient. Alternatively or in addition, the portion of the apparatus that is deliverable into the patient may be delivered through a catheter or other catheter-like tube previously introduced into the patient. The apparatus may be configured so that additional instrumentation can be introduced into the patient over or through the apparatus.

Further features of the invention, its nature and various advantages, will be more apparent from the accompanying drawings and the following detailed description.

BRIEF DESCRIPTION OF THE DRAWINGS

FIG. 1 is a simplified elevational view of an illustrative embodiment of apparatus constructed in accordance with the invention. FIG. 1 shows the tissue anchor structure of the apparatus in an undeployed state.

FIG. 8 is generally similar to FIG. 1, but shows another illustrative embodiment of the invention. FIG. 8 shows the tissue anchor portion of the apparatus in a deployed state.

DETAILED DESCRIPTION

Figure 1:
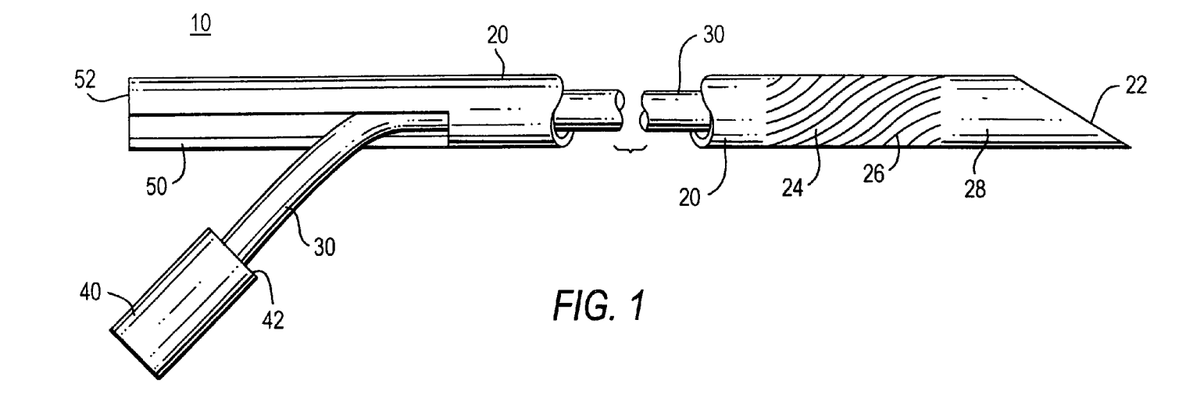
Figure 3:
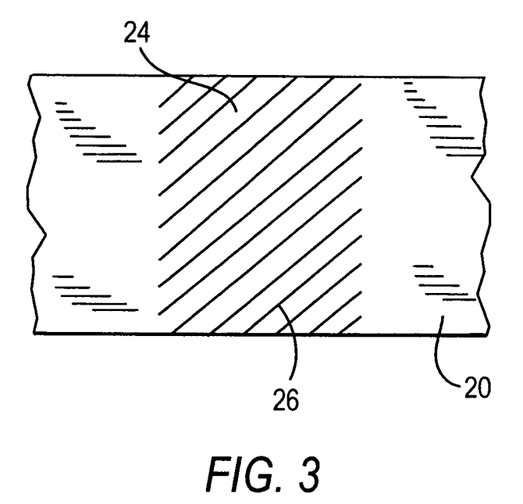
FIG. 3 is a simplified view of a portion of the FIG. 1 apparatus that has been cut longitudinally and laid flat for purposes of illustration.

In the illustrative embodiment shown in FIG. 1, anchor structure 10 (which is shown prior to deployment) includes elongated hollow structure or tubular member 20, a longitudinal member 30 such as a wire disposed (for the most part) inside a lumen of member 20, and a latch member 40 attached to the proximal end of member 30. The distal end 22 of member 20 may be shaped into a point or screw or other shape to facilitate tissue penetration, and/or the distal end of member 30 may accomplish the same. A relatively distal portion of member 20 (proximal of the extreme distal end of that member) is shaped to include a number of spiral strips 24 (intercalated with spiral cuts 26). Strips 24 and cuts 26 spiral in a circumferential direction around member 20 in the manner that relatively steep screw threads would spiral around a rod. (FIG. 3 shows a portion of member 20 cut longitudinally and laid flat to more clearly reveal the pattern of strips 24 and cuts 26.) There is a portion 28 of member 20 distal to strips 24 that is intact (i.e., not cut to produce spiral strips). Similarly, the portion of member 20 proximal to strips 24 is intact (i.e., not cut to produce spiral strips). Thus strips 24 are confined to a relatively distal portion of the length of member 20, generally as shown in FIG. 1.

The distal end of member 30 is secured to the distal portion 28 of member 20 (i.e., distal to strips 24). Alternatively, the distal end of member 30 may be shaped such that motion relative to member 20 is limited to one-way motion, i.e., member 30 can move distally relative to member 20, but it can only move proximally relative to portion 28 until it reaches a stop in portion 28. The more proximal remainder of member 30 is longitudinally or axially slidable along the length of member 20, for the most part inside the lumen of member 20.

Near the proximal end of member 20, that member has a slot 50 in its side that is wide enough for member 30 to come out of that side of member 20.

In the undeployed condition of the apparatus shown in FIG. 1, the distal surface 42 of latch member 40 is distal to the proximal or engagement surface 52 of member 20. In other words, with strips 24 in the relaxed condition shown in FIG. 1, member 30 is not long enough relative to the length of member 20 to permit latch member 40 to be located at the proximal end of member 20. Thus in this condition of the apparatus, latch member 40 and a proximal portion of member 30 are to one side of member 20 outside of slot 50.

Figure 2:
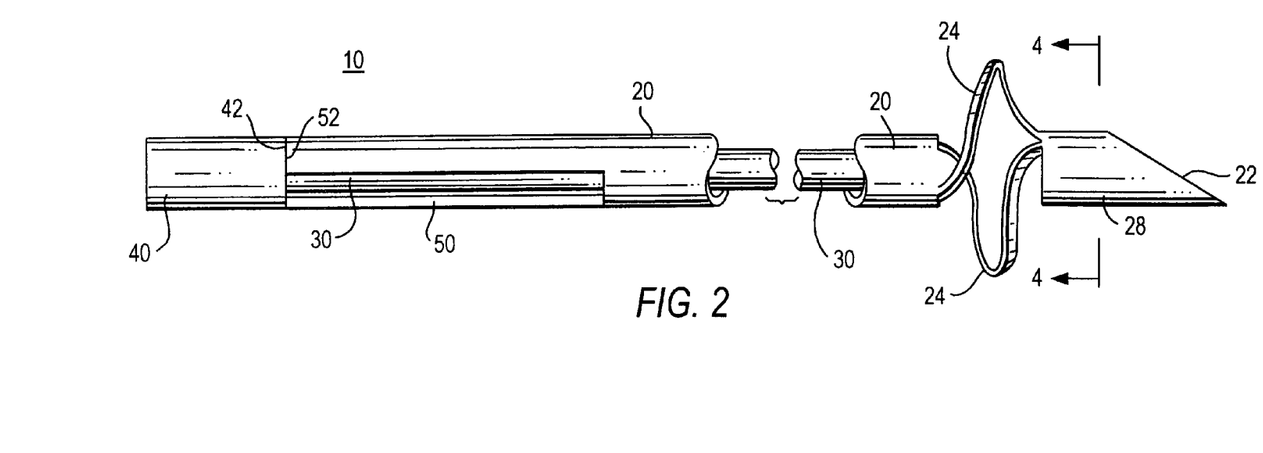
FIG. 2 is similar to FIG. 1, but shows the tissue anchor structure in a deployed state.
Figure 4:
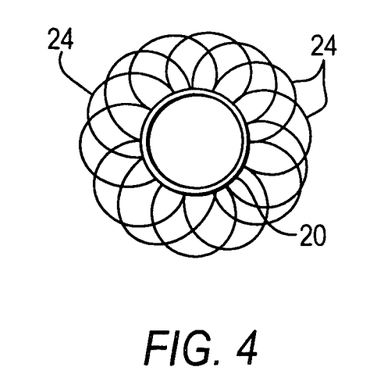
FIG. 4 is a simplified cross sectional view taken along the line 4-4 in FIG. 2.

When it is desired to deploy the anchor feature of structure 10, the proximal portion of member 20 is pushed distally relative to elements 30 and 40. (Alternatively, elements 30 and 40 may be pulled proximally relative to the proximal portion of member 20, or some combination of pushing and pulling may be employed.) This causes the distal portion 28 of member 20 (which is secured to the distal end of member 30) and the portion of member 20 that is proximal to strips 24 to move toward one another. This in turn causes strips 24 to buckle and deflect radially outwardly as shown in representative part in FIG. 2 and in a very simplified way in FIG. 4. FIG. 2 shows only two representative strips 24 to avoid complicating the drawing. FIG. 4 shows a full set of strips 24, but simplifies the representation of each strip to a single line, again to avoid over-complicating the drawing.

When strips 24 have been deflected outwardly as shown in FIGS. 2 and 4, latch member 40 can be aligned with the proximal end of member 20, as is also shown in FIG. 2. In this position, latch member 40 holds strips 24 in their radially outward condition.

When it is no longer desired to have the anchor feature of the apparatus deployed, latch member 40 can be pushed off the proximal end of member 20 toward slot 50. This allows the apparatus to return to the condition shown in FIG. 1. In particular, it allows strips 24 to return to the condition in which they no longer project radially outwardly from the remainder of member 20, but rather collectively form a structure that again has approximately the same outer circumferential size as the remainder of member 20.

An illustrative use of apparatus 10 is to penetrate tissue at a remote location and then provide an anchor in the tissue at that location. For example, the distal tip 22 of member 20 can be pushed into tissue at a remote location with the anchor structure 10 in the condition shown in FIG. 1. The distal portion of the structure is pushed into the tissue until strips 24 (still undeployed as shown in FIG. 1) are below the surface of the tissue. When strips 24 are at the desired depth in the tissue, strips 24 can be deployed as shown in FIG. 2 to prevent the apparatus from being pulled out of the tissue. To release the anchor structure and remove it from the tissue, the apparatus can be returned to the condition shown in FIG. 1. In this condition the apparatus can be easily pulled out of the tissue.

Another illustrative use of the apparatus is to push the undeployed anchor structure all the way through a tissue structure (e.g., the septum between two chambers of the heart). After undeployed strips 24 have been pushed through such a tissue structure, the strips can be deployed as shown in FIG. 2 to prevent the distal portion of the anchor structure from being pulled back into or through the tissue that has been passed through. When it is desired to remove the anchor structure, strips 24 can be undeployed (i.e., returned to the condition shown in FIG. 1) so that the structure can be easily pulled back through the tissue that it initially penetrated.

Still another example of use of the apparatus is as a stop (which can be selectively activated or deactivated). For example, if it is desired to prevent member 20 from penetrating tissue by more than a certain distance, strips 24 can be deployed before or as penetration begins. Penetration stops when deployed strips 24 reach the surface of the tissue being penetrated. If further penetration is subsequently desired, strips 24 can be undeployed and penetration can be continued.

Structure 10 can be constructed with a wide range of different characteristics to satisfy many different needs. For example, the stiffness of strips can be varied widely by varying their width and thickness. As another example, the overall stiffness of the apparatus can be varied by varying such parameters as the size and thickness of members 20 and 30. Structure 10 may be designed for delivery into the body inside a catheter and/or over a guide wire, and for that type of use may be made very thin and laterally flexible. Alternatively, structure 10 may be made bigger and laterally stiffer for other uses in which it needs to be more self-aligning. To facilitate delivery over a guide wire, element 30 may also be tubular so that apparatus 10 can be passed into the patient over the guide wire (i.e., with the guide wire passing along the lumen inside member 30).

The size and strength of the anchor feature can be varied. For example, stiffer strips 24 tend to provide a stronger anchor. Longer strips 24 can be used to provide a larger anchor (e.g., an anchor with a larger circumference when strips 24 are buckled and thereby deployed).

Strips 24 can be located at any distance from distal tip 22 to provide an anchor structure at any desired location along the apparatus.

Spiral strips 24 tend to be preferred because they tend to distribute the stress of buckling along more of the length of each strip, rather than producing stress concentrations at one or a few points along the length of each strip. The angle of inclination (the spiral angle) of the strips can be different in different embodiments.

In addition to providing an anchor in tissue, structure 10 may provide a guideway for introducing other apparatus into a patient. For example, in the embodiment shown in FIGS. 1 and 2, when latch member 40 is latched at the proximal end of member 20 as shown in FIG. 2, latch member 40 is effectively a proximal continuation of member 20 with the same outer cross-sectional size and shape as member 20. Additional apparatus can therefore be passed into the patient along structure 10 (e.g., concentrically around the outside of aligned members 20 and 40). Deployed anchor features 24 hold the distal portion of structure 10 at the desired location in the patient's tissue. This can be used to help ensure that other apparatus introduced into the patient along structure 10 reaches the desired destination in the patient. It can also be used to help provide force (direct force or reaction force) needed by structure 10 and/or any other apparatus introduced into the patient via apparatus 10 in order to perform a procedure on the patient.

Still another possible use of the apparatus is as a temporary or permanent electrical lead and connection to a patient's tissue, e.g., at the location of anchor features 24. For example, structure 10 can be covered with electrical insulation except at strips 24. Electrical current can be conducted to and/or from the patient at the location of deployed strips 24 via other metal components of the apparatus (e.g., member 20). An example of such electrical use of the apparatus is as an electrical lesion generator for ablation of a patient's tissue (e.g., at the location of anchor features 24).

Figure 5:
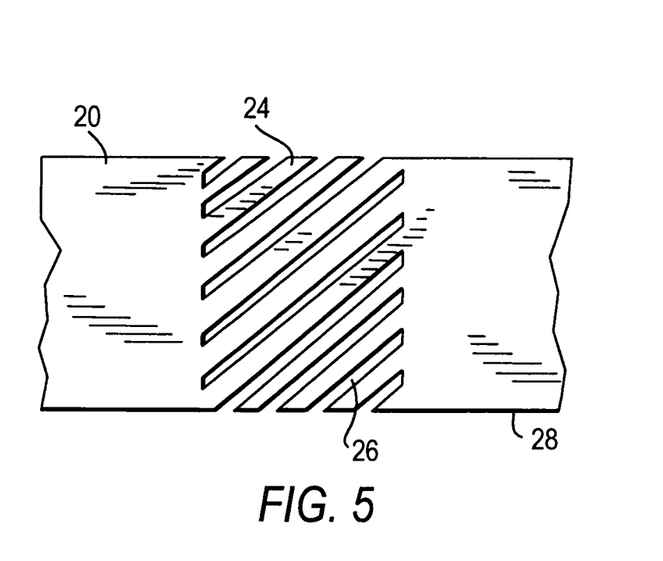
FIG. 5 is similar to FIG. 3 for another illustrative embodiment of the invention.
Figure 6:
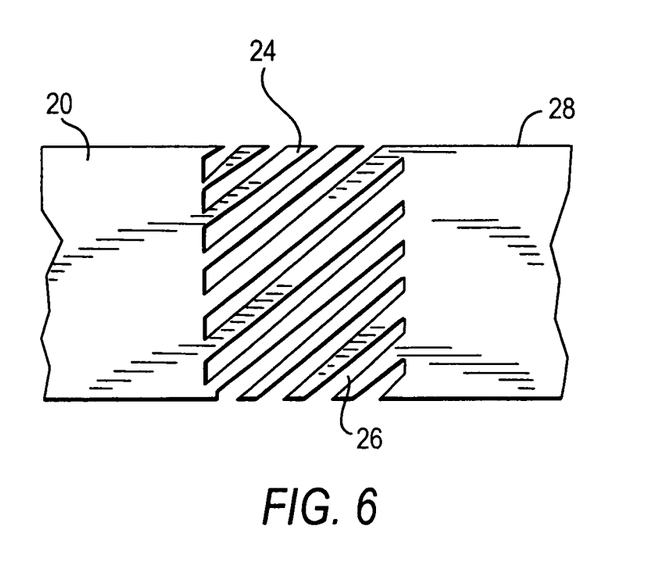
FIG. 6 is similar to FIG. 3 for yet another illustrative embodiment of the invention.
Figure 7:
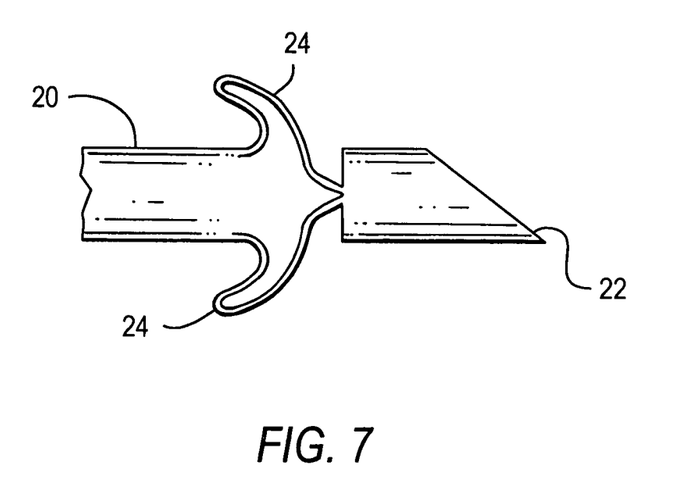
FIG. 7 is similar to a portion of FIG. 2 for an embodiment like that shown in FIG. 6.
Figure 22:
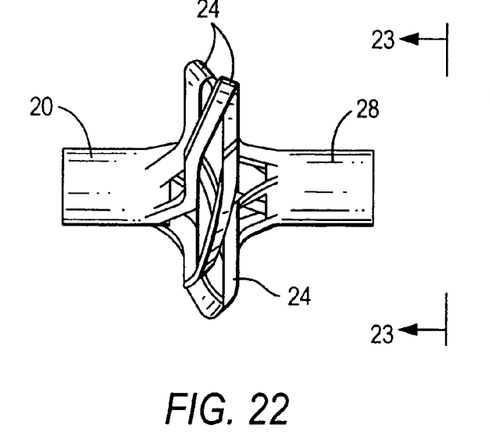
FIG. 22 is a simplified elevational view of a structure of the type shown in FIG. 5 when deployed in accordance with the invention.
Figure 23:
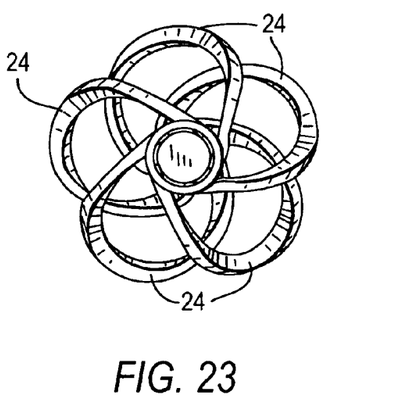
FIG. 23 is a simplified view taken along the line 23-23 in FIG. 22.
Figure 24:
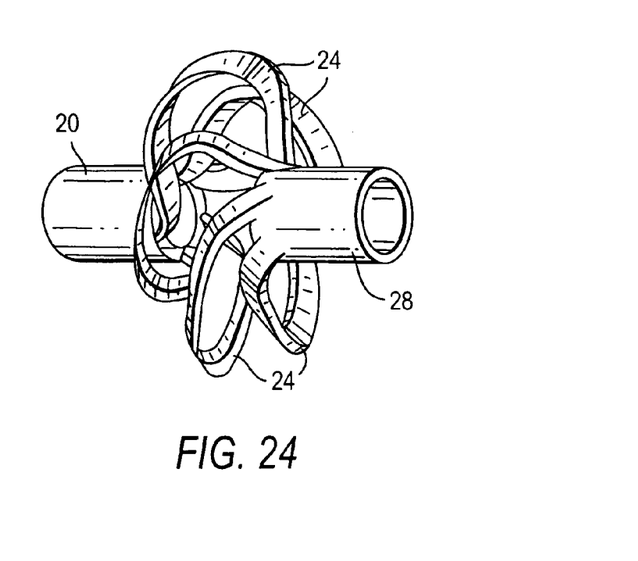
FIG. 24 is a simplified isometric view of what is shown in FIGS. 22 and 23.

Cuts 26 can be made in member 20 in any desired way. Laser cutting is an example. Cuts 26 can be shaped to affect the behavior of the apparatus in any of several ways. For example, FIG. 5 shows an embodiment in which cuts 26 are relatively wide slots, thereby increasing the spacing between strips 24, making the strips narrower, etc. FIGS. 22-24 show several views of a FIG. 5 type anchor structure when deployed. As another example, FIG. 6 shows an embodiment in which cuts 26 are wider toward the left and narrower toward the right. This tends to make strips 24 weaker toward the left and stronger toward the right. A feature like this can be used to give the deployed anchor feature a particular shape. For example, FIG. 7 shows that the deployed strips 24 cooperate to produce a cup-like anchor structure as a result of tapering cuts 26 as shown in FIG. 6. Each strip is more resistant to curvature toward the right where it is stronger. This produces the left-ward opening, cup-like anchor structure shown in FIG. 7. If slots 26 were tapered in the opposite direction from what is shown in FIG. 6, the cup shape of FIG. 7 would face in the opposite direction.

Figure 17:
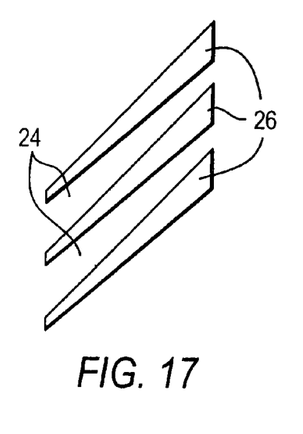
FIGS. 17-21 are each similar to a representative portion of FIG. 3, 5, or 6, and show other examples of possible slot and intervening strip shapes in accordance with the invention.
Figure 18:
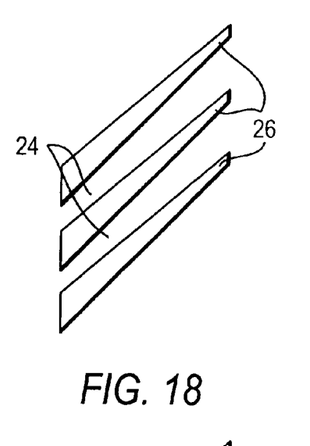
Figure 19:
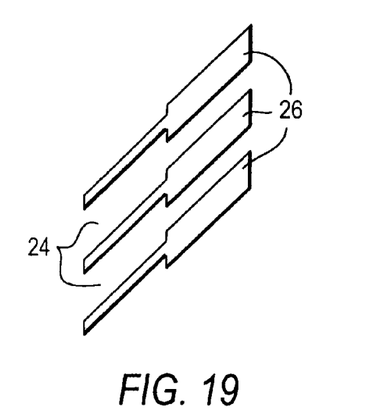
Figure 20:
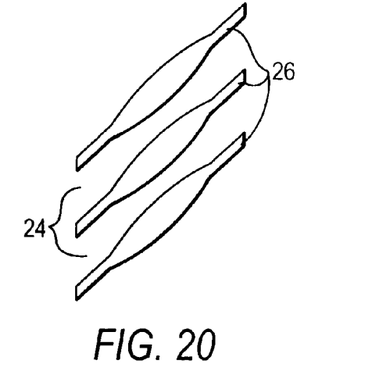
Figure 21:
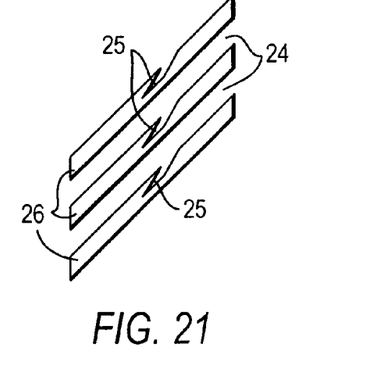

More examples of slot 26 and intervening strips 24 are shown in representative part in FIGS. 17-21. FIG. 17 is similar to FIG. 6, except that in FIG. 17 slots 26 are wider on the right than on the left. Thus in FIG. 17 strips 24 are wider on the left than on the right. This tends to produce a cup-like deployment of strips 24 as shown in FIG. 7, except that the cup will be open from the right rather than from the left as in FIG. 7. FIG. 18 shows a slot and strip pattern similar to FIG. 6. In FIG. 19 the width of slots 26 steps fairly abruptly from relatively narrow on the left to relatively wide on the right. This causes the width of intervening strips 24 to step correspondingly abruptly from relatively wide on the left to relatively narrow on the right. In FIG. 20 a medial portion of each slot 26 gradually widens and then narrows again. This causes the medial portion of each strip 24 to gradually narrow and then widen again. In FIG. 21 each strip 24 has a barb 25 that projects from one side of the strip into the adjacent slot 26. Such barbs 25 can penetrate tissue when strips 24 are deployed. This can be used to increase the tissue holding and/or tissue penetrating power of the deployed anchor structure.

Figure 8:
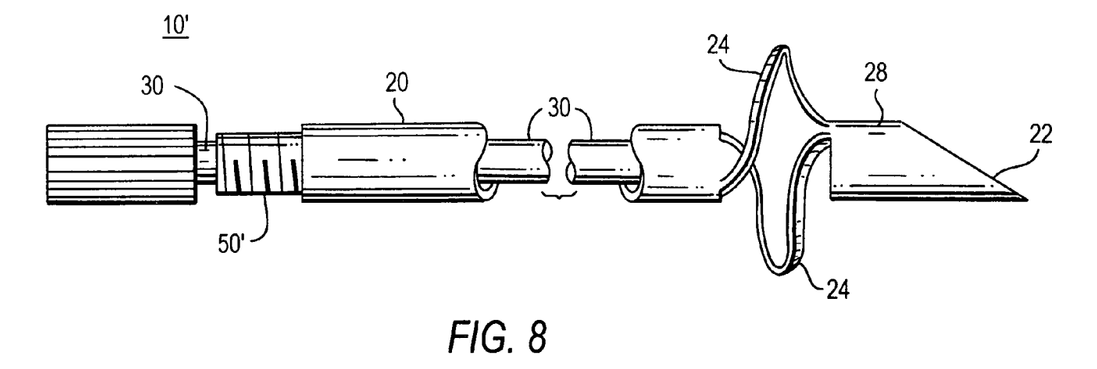
Figure 9:
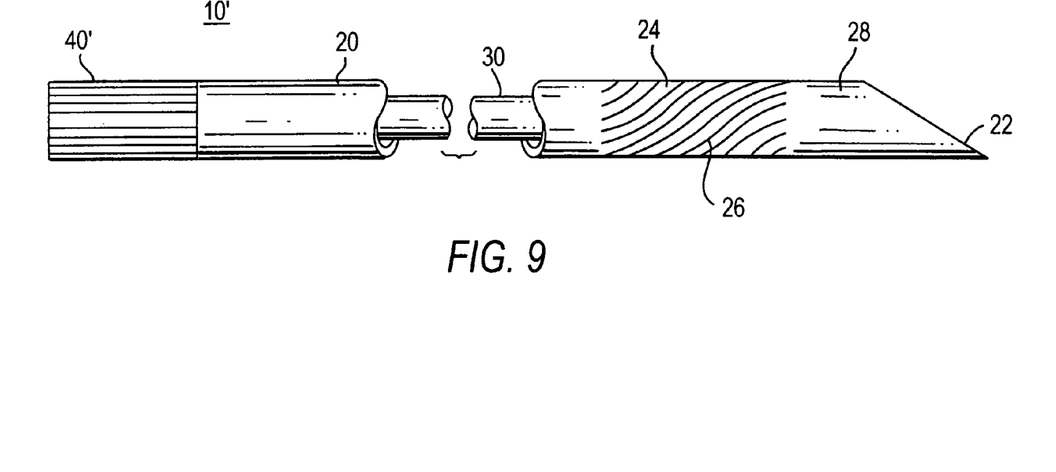
FIG. 9 shows the undeployed state of the FIG. 8 embodiment.

The embodiments shown and described thus far are constructed so that the relaxed state of the apparatus has the anchor feature undeployed. Strips 24 are stressed to buckle them and thereby deploy the anchor feature. This aspect of the operating mode of the apparatus can be reversed, if desired. For example, FIGS. 8 and 9 show another illustrative embodiment 10' in which the unstressed condition of strips 24 is the radially outward, deployed condition as shown in FIG. 7. When it is desired to undeploy the anchor feature, latch member 40' is threaded onto the threaded end 50' of member 20. (In this embodiment, latch member 40' is rotatably secured to the proximal end of member 30.) This pulls the proximal portion of member 20 proximally relative to distal portion 28 (again secured to the distal end of member 30). This in turn causes strips 24 to draw in and straighten out, thereby undeploying the anchor feature as shown in FIG. 9.

An illustrative way to provide embodiments of the type illustrated by FIGS. 8 and 9 is to make member 20 (or at least the relevant portion of member 20) from a nitinol tube, which has been heat-set in the condition shown in FIG. 8. The deployed condition of strips 24 thereby becomes the unstressed or at-rest condition of the apparatus. But the apparatus can be stressed to draw in strips 24 as shown in FIG. 9 when it is desired to undeploy the anchor feature.

Figure 10:
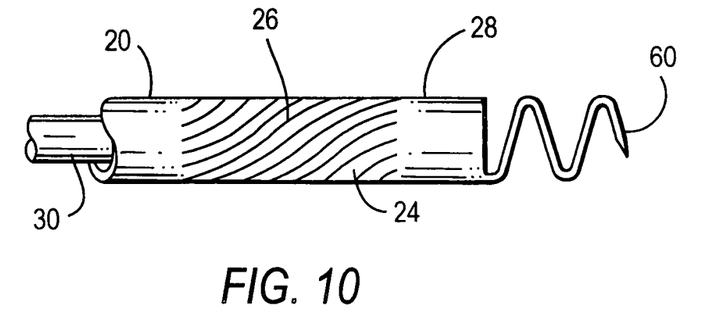
FIG. 10 is similar to a portion of FIG. 1, but shows another illustrative embodiment in accordance with the invention.

As an alternative to push-penetration of tissue as in the previously described embodiments, the distal end of member 20 may include a tissue penetrating screw portion 60 as shown in FIG. 10. In this type of embodiment, after the distal end of screw 60 has contacted tissue, member 20 can be rotated to thread screw 60 into the tissue. In this way screw 60 effectively pulls the distal end of the apparatus into the tissue.

Figure 11:
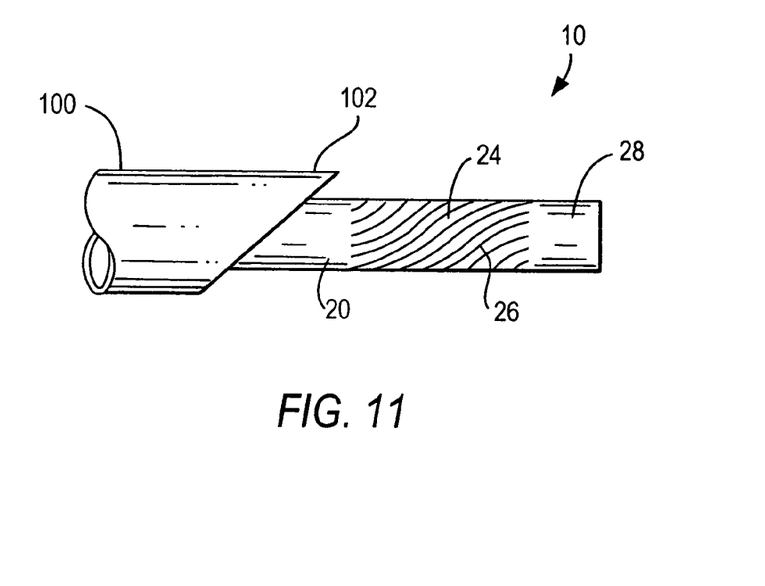
FIG. 11 is similar to a portion of FIG. 1, but shows still another illustrative embodiment in accordance with the invention.

FIG. 11 shows an alternative embodiment in which anchor structure 10 is deployed inside a separate axially-slidable, tissue-piercing structure 100. Before anchor structure 10 is extended from the distal end of structure 100 as shown in FIG. 11, the distal end of structure 100 is used to pierce or penetrate tissue. The distal end 102 of structure 100 is sharpened for that purpose. Then anchor structure 10 can be pushed out of the distal end of structure 100 as shown in FIG. 11 and tissue anchoring strips 24 can be deployed as shown, for example, in FIG. 2. While strips 24 are thus deployed, structure 100 can be pulled off the proximal end of structure 10 and other apparatus for performing another part of a procedure can be exchanged for structure 100 (i.e., guided into the patient along and concentrically around structure 10).

Figure 12:
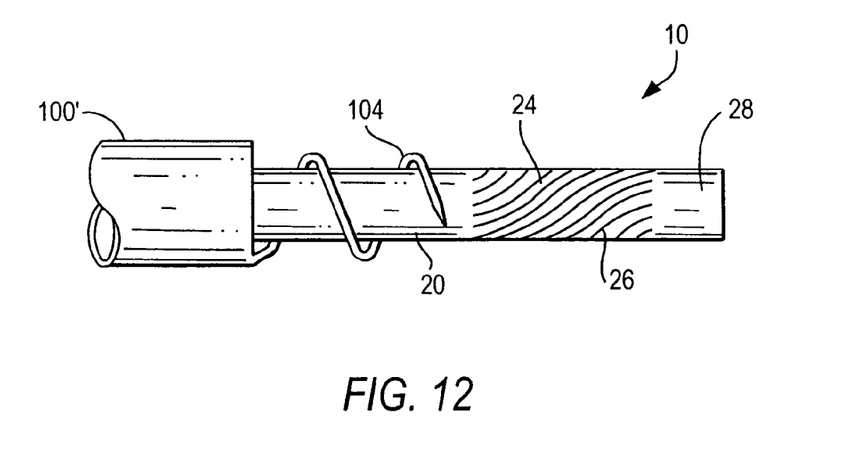
FIG. 12 is similar to a portion of FIG. 1, but shows yet another illustrative embodiment in accordance with the invention.

FIG. 12 shows another alternative embodiment in which tissue penetrating structure 100' leads with a tissue piercing or cutting screw portion 104. In other respects the embodiment of FIG. 12 may be similar to the embodiment of FIG. 11.

Figure 13:
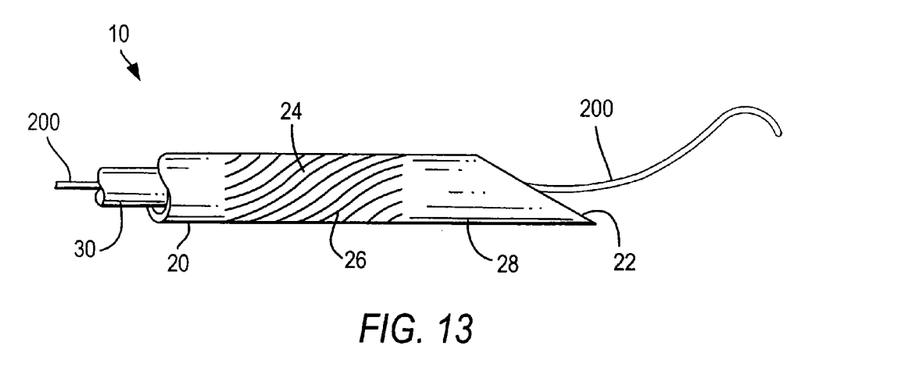
FIG. 13 is similar to a portion of FIG. 1, but shows still another illustrative embodiment in accordance with the invention.

FIG. 13 illustrates the point that structure 10 can be introduced into the patient along a guide wire 200 or the like. Alternatively, element 200 in FIG. 13 may be a wire that is extended from the apparatus after there has been tissue penetration by element 20. In that case wire 200 may be designed to meander after it has exited from structure 10. This effectively gives the apparatus an atraumatic tip because meandering wire 200 prevents the distal end of structure 10 from being pushed farther than it is desired for it to be pushed. As still another or additional possibility, wire 200 can become a guide wire for subsequent procedures (or, as has been mentioned, structure 10 can itself be a guide "wire" for subsequent procedures).

A member that is inside of elements 20 and 30 (like guide wire 200 in FIG. 13) can be a tissue penetrating member, if desired. If that is done, then member 20 can follow the lead of the tissue penetrating member into the tissue, somewhat enlarging the tissue penetration as it goes.

Figure 14:
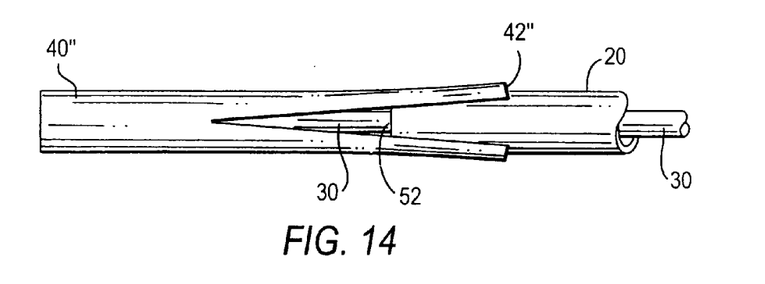
FIG. 14 is similar to another portion of FIG. 1, but shows another illustrative embodiment of the invention.
Figure 15:
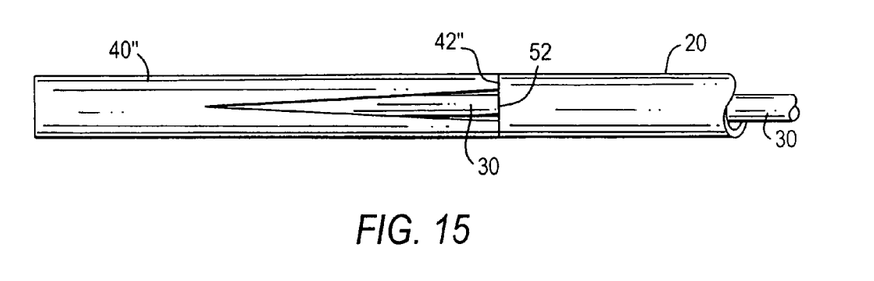
FIG. 15 shows another operating condition of what is shown in FIG. 14 in accordance with the invention.

FIGS. 14 and 15 show another illustrative embodiment of a latching structure 40". In this embodiment latching structure 40" may be a tubular member that is similar in size to tubular member 20. A distal portion of the length of member 40" is cut axially so that some of that portion of member 40" can be resiliently opened to fit around the outside of the proximal end of member 20 as shown in FIG. 14. This corresponds to the condition of the apparatus that is illustrated by FIG. 1, for example. When it is desired to deploy strips 24, member 40" is pulled back proximally until its distal surface 42" closes down again and engages the proximal end 52 of member 20 as shown in FIG. 15. This corresponds to the condition of the apparatus that is illustrated by FIG. 2, for example. The cut in member 40" can spring part way closed to help surfaces 42" and 52 engage one another. To reverse the deployment of strips 24, member 40" can be forced back over the proximal end of member 20 (i.e., back to the condition shown in FIG. 14).

Figure 16:
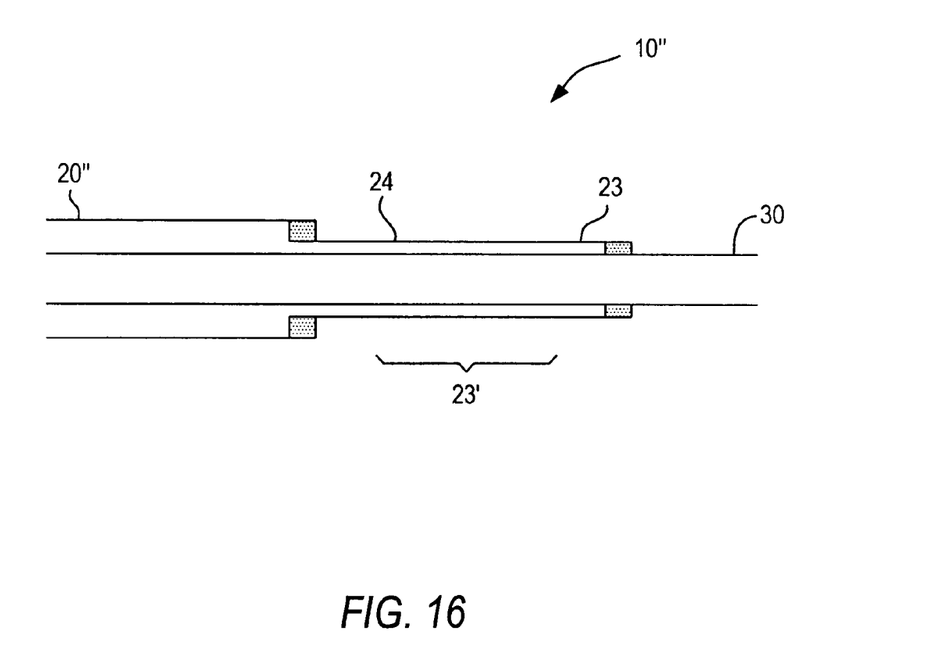
FIG. 16 is a simplified longitudinal sectional view of a portion of yet another illustrative embodiment in accordance with the invention.

Another example of how the anchor structure of this invention can be constructed is shown in FIG. 16 (which, like several of the earlier FIGS., shows only the distal portion of anchor structure 10"). In this embodiment an annular array of flexible members 24 is attached at the distal end to inner member 30, and it is attached at the proximal end to outer member 20". Flexible members 24 can be deployed radially outwardly or pulled radially inwardly by relative axial motion of elements 20" and 30. This type of construction may facilitate the fabrication of structure 24 separately from other elements, with the various parts being assembled later as shown in FIG. 16. In the illustrative embodiment shown in FIG. 16 the component 23 that includes strips 24 also includes an intact tubular portion at each end of the strips. In other words, strips 24 are confined to the intermediate portion of component 23 that is indicated by bracket or brace 23'.

Examples of possible applications of the invention include apparatus for use in crossing the septum of a patient's heart.

Another example of a possible use is in vascular closure. In a use of that kind the radially expandable, distal portion of the apparatus is inserted through the side wall of the vessel to be closed. The expandable portion is then expanded and pulled back slightly against the vessel wall. A clot-promoting agent may be introduced outside the vessel wall. The radially expanded structure helps to keep the clot-promoting agent from actually entering the vessel. The radially expandable structure may be covered with a flexible membrane such as silicone to help keep the agent out of the vessel. The expandable structure can be collapsed and withdrawn from the patient at the appropriate time.

Still another example of possible use of the invention is as an anchor in a body conduit such as a blood vessel. This use may not involve tissue penetration. Rather, the expandable portion of the apparatus is expanded at a location in a vessel that is somewhat smaller in diameter than the apparatus when expanded. The expanded apparatus engages the side wall of the vessel and provides an anchor in the vessel.

It has also been mentioned that the apparatus can be used as an anchor that is embedded in tissue.

Although flexible members 24 are preferably provided so that they spiral about a central longitudinal axis of the apparatus, they could be provided so that they are parallel to the central longitudinal axis (although this is not the presently preferred embodiment for reasons that are mentioned earlier). Flexible members 24 preferably form a single layer of deflectable components. They are preferably not part of a multi-layered structure such as a braid of wires. The presently most preferred construction of the anchor structure is a single tube with intact end portions and an intermediate portion (between the end portions) that has been cut or slotted at several circumferentially spaced locations around the tube. The cuts or slots preferable spiral, but can be longitudinal of the tube in a presently less preferred embodiment. This type of construction (i.e., cutting or slotting an intermediate portion of a tube) has the advantage of making the anchor structure an integral, one-piece component of the apparatus. In other words, each of strips 24 is integral (one piece) with an intact tube at each end of each strip. A presently less preferred construction is to make each of strips 24 as a length of wire that extends between two axially aligned but spaced tubes.

The various components of the apparatus can be made of any of a wide range of materials and in any of many different ways. For example, member 20 may be made of a metal such as nitinol or stainless steel. Member 30 may also be made of metal. Certain plastics may be suitable for all or portions of member 20, including strips 24. A medial portion of member 20 (e.g., between the region of strips 24 and the region of slot 50) may be formed of a spiral-wound metal wire to increase lateral flexibility of the structure. As has been mentioned, member 30 may be hollow if, for example, it is desired to pass a guide wire through the apparatus. The portion of the apparatus that includes strips 24 may be made as a subassembly that is initially separate from other parts of the apparatus (including other portions of member 20). For example, this part of member 20 may be made separately from nitinol, and then attached to a remainder of member 20 that is made of stainless steel and/or of spiral wound wire. FIG. 16 shows an example of an embodiment that can be constructed in this way. Strips 24 may initially be separate members that are welded at their ends to tubes that form adjacent portions of member 20.

It will be understood that the foregoing is only illustrative of the principles of the invention, and that various modifications can be made by those skilled in the art without departing from the scope and spirit of the invention. For example, the types of latching or other connection between elements 20 and 40 or 20 and 40' that are shown herein are only examples, and other arrangements can be used instead if desired.

The invention claimed is:

1. Selectively deployable tissue anchor apparatus, comprising:
   a tubular member having an engagement surface, a proximal portion, a distal portion, and an intermediate portion disposed between the proximal and distal portions, the intermediate portion including a plurality of flexible strips connecting the proximal and distal portions, the plurality of strips having a distal end, a first condition in which the intermediate portion has a first circumference and a second condition in which the intermediate portion has a second circumference larger than the first circumference, the tubular member having a relaxed length in the first condition between the distal end of the strips and the engagement surface, the tubular member having a compressed length in the second condition between the distal end of the strips and the engagement surface, the tubular member having a lumen extending therethrough in a longitudinal direction, the lumen having a transverse cross-section in the proximal portion;

a longitudinal member having a proximal end, and a distal end connected to the distal portion of the tubular member, the longitudinal member being axially slidable relative to the proximal and intermediate portions of the tubular member, whereby axial movement of the longitudinal member relative to the proximal portion in the proximal direction causes the strips to move toward the second condition, and axial movement of the longitudinal member relative to the proximal portion in the distal direction causes the strips to move toward the first condition; and a latch member disposed on the longitudinal member, the latch member having a transverse cross-section that is larger than the transverse cross-section of the lumen so that the latch member is never freely slidable in the lumen of the proximal portion, the longitudinal member having a fixed length between the distal end of the longitudinal member and the latch member whenever the latch member is axially aligned with the tubular member, the fixed length of the longitudinal member being less than the relaxed length of the tubular member such that the tubular member interferes with the axial alignment of the latch member with the tubular member in the first condition, and the fixed length of the longitudinal member being greater than the compressed length of the tubular member such that the latch member may be axially aligned with the tubular member in the second condition, whereby the latch member is able to engage the engagement surface of the tubular member in the second condition to fix the plurality of strips in the second condition.

2. The apparatus defined in claim 1, wherein the strips are resiliently biased to extend between the proximal and distal portions of the tubular member without substantial radial outward projection from the proximal and distal portions.

3. The apparatus defined in claim 1, further comprising:
a tissue penetrating structure on an end of the distal portion of the tubular member remote from the strips.

4. The apparatus defined in claim 1, wherein the tubular member and at least a portion of the longitudinal member adjacent to the tubular member are deliverable into a patient via a body conduit of the patient.

5. The apparatus defined in claim 4, wherein the tubular member and the portion of the longitudinal member are deliverable into the patient over a guide wire previously introduced into the patient.

6. The apparatus defined in claim 4, wherein the tubular member and the portion of the longitudinal member are deliverable into the patient through a catheter previously introduced into the patient.

7. The apparatus defined in claim 4 further comprising:
additional instrumentation configured for introduction into the body conduit around the tubular member.

8. The apparatus defined in claim 1 wherein the strips are configured to inhibit axial movement of the apparatus relative to tissue adjacent to the strips when the strips are in the second condition.

9. The apparatus defined in claim 8, wherein the strips are configured to permit axial movement of the apparatus relative to the tissue adjacent to the strips when the strips are in the first condition.

10. The apparatus defined in claim 1, wherein the proximal and distal portions of the tubular member and the plurality of strips are formed integrally with one another.

11. The apparatus defined in claim 1, further comprising a slot formed in the longitudinal direction in the proximal portion of the tubular member, the slot having a width sized for the longitudinal member to pass through in the first condition.

12. The apparatus defined in claim 1, wherein the intermediate portion defines a tube surrounding the longitudinal member wherein the plurality of strips are in the first condition.

* * * * *